US007125474B2

(12) United States Patent
Beckmann et al.

(10) Patent No.: US 7,125,474 B2
(45) Date of Patent: Oct. 24, 2006

(54) PROCESS FOR REMOVING 2-BUTANOL FROM TERT-BUTANOL/WATER MIXTURES

(75) Inventors: Andreas Beckmann, Recklinghausen (DE); Dieter Reusch, Marl (DE)

(73) Assignee: Oxeno Olefinshemie GmbH, Marl (DE)

( * ) Notice: Subject to any disclaimer, the term of this patent is extended or adjusted under 35 U.S.C. 154(b) by 195 days.

(21) Appl. No.: 10/790,706

(22) Filed: Mar. 3, 2004

(65) Prior Publication Data

US 2004/0182691 A1 Sep. 23, 2004

(30) Foreign Application Priority Data

Mar. 22, 2003 (DE) ................................ 103 12 917

(51) Int. Cl.
*B01D 3/42* (2006.01)
*C07C 29/82* (2006.01)

(52) U.S. Cl. ................... 203/2; 203/3; 203/18; 203/77; 203/80; 203/DIG. 9; 568/913

(58) Field of Classification Search .................... 203/2, 203/3, 18, 74, 77, 80, 99, DIG. 9, DIG. 19; 568/913
See application file for complete search history.

(56) References Cited

U.S. PATENT DOCUMENTS 4,371,427 A * 2/1983 Holler et al. .................. 203/3
4,902,385 A * 2/1990 Osterburg .................... 203/96
5,085,739 A * 2/1992 Berg et al. .................... 203/18
5,332,478 A * 7/1994 Berg ........................... 203/58
5,368,699 A * 11/1994 Rhiel et al. .................... 203/2
5,658,435 A * 8/1997 Berg ........................... 203/57
5,759,359 A * 6/1998 Berg ........................... 203/57
5,985,100 A 11/1999 Aron et al.
6,413,378 B1 * 7/2002 Kanauchi et al. .............. 203/1

OTHER PUBLICATIONS

Derwent Publications, AN 1986-039691, XP-002279550, JP 60-260531, Dec. 23, 1985.
Chinese Office Action w/English Translation as received in corresponding Chinese Application No. 200310120351 (Mar. 31, 2006).
Li Fengyun, Journal of Fushun Petroleum College, 18(4): 28-30 w/English Abstract.
Guo Yufeng et al, Petrochemical Technology and Application, 17(2):114-117 w/English Abstract.

* cited by examiner

*Primary Examiner*—Virginia Manoharan
(74) *Attorney, Agent, or Firm*—Oblon, Spivak, McClelland, Maier & Neustadt, P.C.

(57) ABSTRACT

The invention relates to a process for separating 2-butanol from an industrial mixture which includes 2-butanol, tert-butanol and water by separating water from the industrial mixture by distillation to obtain a distillate, wherein the distillate has, in terms of the 2-butanol, tert-butanol and water in the industrial mixture, a proportion by mass of water, which at a pressure, is greater than the limit concentration of the distillation boundary line connecting an azeotrope of tert-butanol and water; and an azeotrope of 2-butanol and water; subsequently changing the pressure so that the mixture has, in terms of the 2-butanol, tert-butanol and water in the distillate, a proportion by mass of water which is less than the limit concentration of the distillation boundary line connecting the distillation boundary line connecting an azeotrope of tert-butanol and water; and an azeotrope of 2-butanol and water; and subsequently distilling the mixture at the same pressure into a stream comprising 2-butanol and a stream comprising tert-butanol and water.

21 Claims, 2 Drawing Sheets

PROCESS FOR REMOVING 2-BUTANOL FROM TERT-BUTANOL/WATER MIXTURES

BACKGROUND OF THE INVENTION

1. Field of the Invention

The present invention relates to a process for separating secondary butanol (also referred to as 2-butanol or SBA below) from tert-butanol/water mixtures which are obtained in the dissociation of tert-butanol (TBA), in particular tert-butanol prepared from industrial C4-hydrocarbon mixtures, into isobutene and water.

2. Discussion of the Background

Isobutene is a starting material for the production of butyl rubber, polyisobutylene, isobutene oligomers, branched C5-aldehydes and C5-carboxylic acids. It is also used as an alkylating agent and as an intermediate for the preparation of peroxides.

In industrial streams, isobutene is present together with saturated and unsaturated C4-hydrocarbons. Isobutene cannot be separated economically from these mixtures by distillation because of the small boiling point difference or the very low separation factor between isobutene and 1-butene. Isobutene is therefore isolated from industrial hydrocarbon mixtures by converting isobutene into a derivative which can easily be separated off from the remaining hydrocarbon mixture and redissociating the isolated derivative into isobutene and the derivative-forming agent.

The following procedure is usually employed to separate isobutene from C4 fractions, for example the C4 fraction from a steamcracker. After the major part of the multiply unsaturated hydrocarbons, mainly butadiene, has been removed by extraction (or extractive distillation) or selective hydrogenation to linear butenes, the remaining mixture (raffinate I or hydrogenated cracking C4) is reacted with alcohol or water. Use of methanol as alcohol gives methyl tert-butyl ether (MTBE) and use of water gives tert-butanol (TBA). After they have been separated off, both products can be redissociated to give isobutene in a reversal of their formation.

The dissociation of TBA is easier to carry out than the dissociation of MTBE and gives smaller amounts of by-products and is thus the preferred method of isolating isobutene. The dissociation of TBA is preferably carried out in the gas or liquid phase in the presence of an acid with partial conversion of TBA.

If hydrocarbon streams containing isobutene, in which linear butenes are also present are used for preparing TBA from isobutene, small amounts of 2-butanol (SBA) are also formed.

Whether this presents any further problem depends on how the resulting reaction mixture is worked up to give pure TBA or a TBA/water azeotrope. Owing to the low 2-butanol content of the reaction mixture, the maximum permissible 2-butanol concentration of, for example, 0.2% by mass in the TBA or in the TBA/water azeotrope is not exceeded.

If, however, the industrial TBA or TBA/water azeotrope is partially dissociated into isobutene and water, separating off the isobutene formed results in a TBA/water mixture enriched in 2-butanol (SBA). This mixture is unsuitable for the preparation of commercial quality TBA or TBA/water azeotrope without 2-butanol being separated off. It is likewise not practical to prepare isobutene from this mixture, because an increasing 2-butanol content also results in an increase in the concentration of linear butenes in the isobutene, so that the specification of the latter cannot be achieved. It is therefore necessary to discharge part of the 2-butanol while avoiding losses of TBA.

In a process for separating SBA from mixtures of SBA, TBA, and water without losses of TBA, however, it is difficult to separate by distillation since this three-component system displays a distillation boundary line which connects the binary water/TBA azeotrope at about 11% by mass of water (the literature reports values at atmospheric pressure of from 10 to 12.5% by mass) (point H in FIG. 1) and the binary water/SBA azeotrope at about 28% by mass of water (the literature reports values at atmospheric pressure of from 26.7 to 32% by mass) (point J in FIG. 1). This distillation boundary line separates two distillation fields. The above three-component system, shown in FIG. 1, thus displays two distillation fields: distillation field 1 in the region A-H-J-A and distillation field 2 in the region H-E-D-J-H. In the distillation field 1, the high boiler is water, the low boiler in this region is the TBA/water azeotrope and the intermediate boiler is the SBA/water azeotrope which cannot be separated off in pure form.

To discharge SBA from an integrated TBA-isobutene plant, it is most economical to use the stream which is richest in SBA for this purpose. However, the streams obtained in the dissociation of TBA have a relatively low SBA content. They usually have compositions lying in the distillation field 1. These streams usually further comprise small amounts of additional substances whose presence need not, however, be considered in this context. If an attempt is made to work up such a mixture having a composition in the region of distillation field 1 by distillation, it is possible either to isolate pure water as high boiler and a mixture of SBA/TBA/water as top fraction or else obtain the TBA/water azeotrope as lowest-boiling mixture in the distillate from a column and obtain a higher-boiling mixture comprising SBA/TBA/water with a high water content at the bottom. Thus, for mass balance reasons and owing to the unfavorable position of the distillation lines, the SBA content cannot be increased sufficiently for discharge of this stream to be economically viable. The miscibility gap in the system (cf. FIG. 1: C-F-G-C) can also not be used economically for separation of the components or increasing their concentration.

SUMMARY OF THE INVENTION

It has surprisingly been found that SBA can be separated off from a production stream which comprises water, SBA and TBA and whose composition lies in the region of distillation field 1, in particular a production stream which is enriched in SBA, virtually without losses of TBA when the feed mixture is depleted in water by means of a single-stage or multistage distillation process so that when the pressure is changed the composition of the mixture obtained in this way is then located in the region of the distillation field 2 and this mixture can thus be separated by distillation into SBA and a TBA/water mixture.

As a result of the pressure change, the position of the distillation boundary line moves from the region B-C at low pressure via approximately H-J (the precise position of the end point is located between C and I) at intermediate pressures to B-I at high pressure. Thus, it is possible firstly to approach the boundary H-J by distillation in the distillation field 1 and, after changing the pressure, separate off essentially pure SBA in the distillation field 2 described by the boundary B-C at low pressure or B-I at high pressure.

The invention accordingly provides a process for separating SBA from an industrial mixture which comprises SBA, TBA and water and in which the proportion by mass of water is greater than the limit concentrations of the distillation boundary line connecting the two azeotropes TBA/water and SBA/water, i.e. the SBA/TBA/water composition of the mixture lies in the region of the distillation field 1, wherein, in a first step, water is separated off from the mixture by means of a distillation process in such an amount that the distillate obtained has, in terms of its SBA/TBA/water composition, a proportion by mass of water which at a predetermined pressure is just greater than the limit concentration of the distillation boundary line connecting the two azeotropes TBA/water and SBA/water, i.e. in terms of its SBA/TBA/water composition lies in the region of distillation field 1, and in a second step, the pressure is subsequently changed so that the mixture has, in terms of its SBA/TBA/water composition, a proportion by mass of water which at a predetermined pressure is less than the limit concentration of the distillation boundary line connecting the two azeotropes TBA/water and SBA/water at this pressure and the mixture is separated by distillation at this pressure into a stream comprising SBA and a stream comprising predominantly TBA and water.

Thus, the SBA is separated off in the process of the invention by means of a combination of two distillation steps, with the pressure being changed between these steps.

The process of the invention is based on the fact that pressure, volume and temperature are all necessary to describe the state of a system, with the individual parameters in multiphase systems being dependent on the concentration of the individual components. The points H and J shown in FIG. 1 apply at a first approximation only at pressures in the region of atmospheric pressure. At higher pressures, the distillation boundary line shifts and connects the points B and I; at lower pressures, the distillation boundary line shifts and connects the points B and C. It is thus possible, at a constant composition, to increase or reduce the pressure so that this composition lies in the distillation field 2 and SBA can therefore be separated off from the mixture by distillation. For this to be successful, the composition of the mixture has to be adjusted in a first distillation step so that although it lies in the distillation field 1 it is at the same time in the field bounded by the lines connecting the points B, H, J and C or the points B, H and I.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

The process of the invention makes it possible to separate SBA from mixtures which comprise SBA, TBA and water and in which the proportion by mass of water is greater than the limit concentrations of the distillation boundary line connecting the two azeotropes TBA/water and SBA/water, so that they cannot be separated purely by distillation. The use of the process of the invention enables the use of entrainers or other extraneous substances to be dispensed with, so that a costly removal of these auxiliaries can be avoided and there is no risk of contamination of the products by these auxiliaries during the work-up.

In the process of the invention for separating SBA from an industrial mixture which comprises SBA, TBA and water and in which the proportion by mass of water is greater than the limit concentrations of the distillation boundary line connecting the two azeotropes TBA/water and SBA/water, i.e. the SBA/TBA/water composition of the mixture lies in the region of the distillation field 1, water is, in a first step, separated off from the mixture by means of a distillation process in such an amount that the distillate obtained has, in terms of its SBA/TBA/water composition, a proportion by mass of water which at a predetermined pressure is just greater than the limit concentration of the distillation boundary line connecting the two azeotropes TBA/water and SBA/water, i.e. in terms of its SBA/TBA/water composition lies in the region of the distillation field 1, and, in a second step, the pressure is subsequently changed so that the mixture has, in terms of its SBA/TBA/water composition, a proportion by mass of water which at a predetermined pressure is less than the limit concentration of the distillation boundary line connecting the two azeotropes TBA/water and SBA/water at this pressure and the mixture is separated by distillation at this pressure into a stream comprising SBA and a stream comprising predominantly TBA and water. The change in the pressure shifts the distillation boundary line in such a way that the mixture obtained in the first step has a composition which after the pressure change lies in the distillation field 2.

Figure 1:
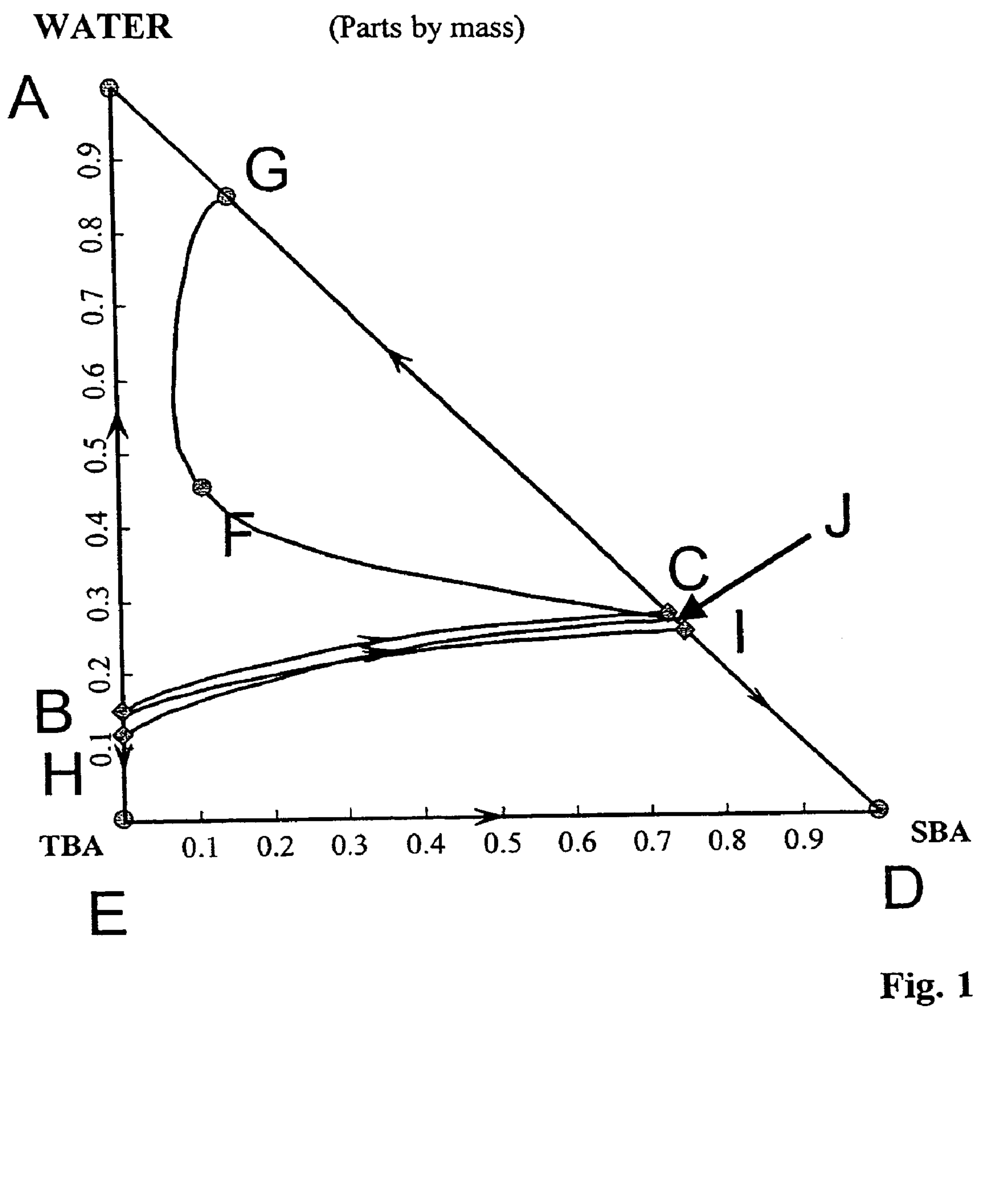
FIG. 1 depicts relative SBA, TBA, and water, in parts by mass, and the azeotropes water/TBA and water/SBA in a distillation of a mixture containing SBA, TBA, and water. Distillation boundary lines which defined distillation fields 1 and 2 are indicated.

As used herein, "distillation boundary line connecting an azeotrope of tert-butanol and water and an azeotrope of 2-butanol and water" means the line which connects the binary water/TBA azeotrope at about 11% by mass of water (the literature reports values at atmospheric pressure of from 10 to 12.5% by mass) (point B in FIG. 1) and the binary water/SBA azeotrope at about 28% by mass of water (the literature reports values at atmospheric pressure of from 26.7 to 32% by mass) (point C in FIG. 1). This distillation boundary line separates two distillation fields. The above three-component system, shown in FIG. 1, thus displays two distillation fields: distillation field 1 in the region A-B-C-A and distillation field 2 in the region B-E-D-C-B. In the distillation field 1, the high boiler is water, the low boiler in this region is the TBA/water azeotrope and the intermediate boiler is the SBA/water azeotrope which cannot be separated off in pure form.

The removal of the water in the first step of the process of the invention can be carried out in a single-stage or multi-stage, in particular single-stage or two-stage, distillation process. Preference is given to separating off the water in the first stage by means of a distillation column.

It can be advantageous to carry out the distillation process in the first step at a pressure of from 0.05 to 15 $bar_{abs.}$ (bara). Only the TBA/water azeotrope displays a minimum in the water concentration as the pressure increases (at about 1 bar); in the case of the SBA/water azeotrope, the water concentration decreases monotonically with increased pressure. The distillation process in the first step is therefore preferably carried out at a pressure of from 0.5 to 5 bara, in particular from 0.6 to 2 bara. The pressure at which the distillation process of the second step is carried out is preferably greater than that in the first step by a factor of at least 2, particularly preferably at least 3. When the process is carried out with a reduction in pressure, the pressure in the first step is preferably greater than that in the second step by a factor of at least 2, particularly preferably at least 3.

If the distillation process in the first step is carried out at a pressure of from 0.7 to 5 bara, it has been found to be advantageous for the pressure in the second step to be reduced to from 0.05 to <0.7 bara and the removal by distillation of the SBA to be carried out at this pressure or for the pressure in the second step to be increased to >5 to 15 bara and the removal by distillation of the SBA to be carried out at this pressure. Particularly in the case of SBA concentrations in the range from 0.001 to 30% by mass, the pressure range can also be changed so that the first process step is carried out at a pressure of from 0.4 to 5 bara and the second process step is carried out at a pressure of from 5 to 15 bara, in particular from 5 to 10 bara; in such a case, the pressures should again differ by a factor of at least 2. This is made possible by the end point B or H of the boundary of the distillation fields 1 and 2 at moderate pressures (from 0.5 to 5 bara, in particular from 0.6 to 2 bara) being close to point H and at pressures of less than 0.5 bara and greater than 5 bara being close to point B. The end point C migrates continually in the direction of end point I from low to high pressures.

The water separated off as residue in the distillation process of the first step preferably has a content of organic constituents of less than 10% by mass, preferably less than 5% by mass and very particularly preferably from 3 to 0.05% by mass, in particular of TBA. Smaller values down to 0.001% by mass can also be achieved, but this is usually not necessary and not economically viable. TBA and SBA can be separated off together from the aqueous residue to leave pure or virtually pure water. This separation can, for example, be carried out purely by distillation, since the mixture has a composition in the region of distillation field 1 and pure or virtually pure water can be obtained as high boiler and a mixture of SBA/TBA/water can be obtained as top fraction in a distillation. The mixture obtained as top fraction can be recirculated either in its entirety or in part after discharge of a substream to the first step of the process of the invention for water to be separated off again.

If appropriate, all or some of the residue can be used directly, for example as process water in a plant for synthesizing TBA.

In the distillation process in the second step of the process of the invention, an SBA-containing stream comprising 2-butanol and possibly high boilers is obtained as bottom product. The TBA content of this 2-butanol-containing stream which has been separated off by distillation in the second step from the distillate obtained in the first step is preferably less than 2% by mass, preferably less than 1.7% by mass. A stream comprising TBA and water, which may also contain low boilers, is taken off as top product. The 2-butanol content of the top product is preferably less than 4% by mass, in particular less than 3% by mass. At the bottom of the column, 2-butanol which is free or virtually free of high boilers can be obtained by taking off the 2-butanol from the vapor phase of the vaporizer or in gaseous or liquid form as side stream in the stripping section of the column. Part of the TBA- and water-containing stream obtained as top product in the second step can be mixed with the distillate obtained in the first step and used as feed to the fractional distillation of the second step.

The TBA fractions which are separated from the mixture by means of the process of the invention and are obtained as distillate in the second step of the process can be employed for known purposes. For example, they can serve as starting material for the preparation of isobutene. Any low boilers present therein can be separated off by distillation.

The 2-butanol which has been separated off can be utilized for customary industrial applications. Thus, for example, it can be used as precursor for methyl ethyl ketone, as solvent for surface coatings and resins, as a constituent of brake fluids and as a constituent of cleaners. Furthermore, it is employed in the production of fragrances, dyes and wetting agents.

The fractional distillations of streams obtained in the process of the invention, in particular the distillate from the first process step, can be carried out in one or more columns provided with internals which may be trays, rotating internals, random packing and/or structured packing. Preference is given to carrying out both the distillation process of the first step and the distillation process of the second step in a single column per step.

In the case of column trays, the following types can be used:

trays having holes or slits in the plate;

trays having necks or chimneys which are covered by bills, caps or hoods;

trays having holes covered by movable valves in the plate;

trays having a special construction.

In columns having rotating internals, the internal reflux is either sprayed by means of rotating funnels or is spread as a film over a heated tube wall by means of a rotor.

Randomized packings of various packing elements can be used in the columns employed in the process of the invention. They can be made of virtually any materials, e.g. steel, stainless steel, copper, carbon, stoneware, porcelain, glass, plastics, etc., and have various shapes, e.g. spheres, rings having smooth or profiled surfaces, rings having internal webs or holes in the wall, wire mesh rings, saddles and spirals.

Packing having a regular geometry can comprise, for example, sheets or woven meshes of metal or plastic. Examples of such packing are Sulzer Gewebepackungen B X, Sulzer Lamellenpackungen Mellapak made of sheet metal, high-performance packing such as MellapakPlus, structured packing from Sulzer (Optiflow), Montz (BSH) and Kühni (Rombopak).

The column used for the preliminary dewatering of the industrial mixture used in the first step of the process of the invention preferably has from 3 to 50 theoretical plates, in particular from 6 to 40 theoretical plates. The feed plate depends on the composition of the mixture in distillation field 1. The feed is preferably introduced onto the 2nd to 45th, counted from the top, theoretical plate, in particular onto the 3rd to 35th theoretical plate (in this context, theoretical plates correspond to theoretical distillation stages).

The distillation in the second step of the process of the invention, in which the SBA is separated off, is preferably carried out in a column having from 5 to 70 theoretical plates, in particular from 10 to 60 theoretical plates. The feed plate again depends on the composition of the mixture and is preferably the 2nd to 55th, counted from the top, theoretical plate, in particular the 3rd to 35th theoretical plate.

The operating pressure of the columns for carrying out the first and second process steps is preferably from 0.05 to 15 $bar_{abs.}$ (bara). As described above, the pressure in the column for carrying out the second process step should be higher or lower than the pressure in the column for carrying out the first process step.

The process of the invention enables 2-butanol to be separated off from any ternary mixtures of TBA, SBA and water lying in the distillation field 1 without losses of TBA. This succeeds even when the mixtures further comprise up to 5% by mass of high boilers (e.g. C8- or C12-hydrocarbons formed by oligomerization of isobutene, C8-alcohols) and/or low boilers (e.g. isobutene or other C4-hydrocarbons). Thus, 2-butanol, in particular 2-butanol mixtures having a tert-butanol content of less than 2% by mass, preferably less than 1.7% by mass, can be prepared by means of the process of the invention.

In particular, TBA streams enriched in 2-butanol from plants in which isobutene is prepared from TBA by elimination of water are used in the process of the invention. These streams usually further comprise C4-hydrocarbons and downstream products of C4-olefins as additional components.

Figure 2:
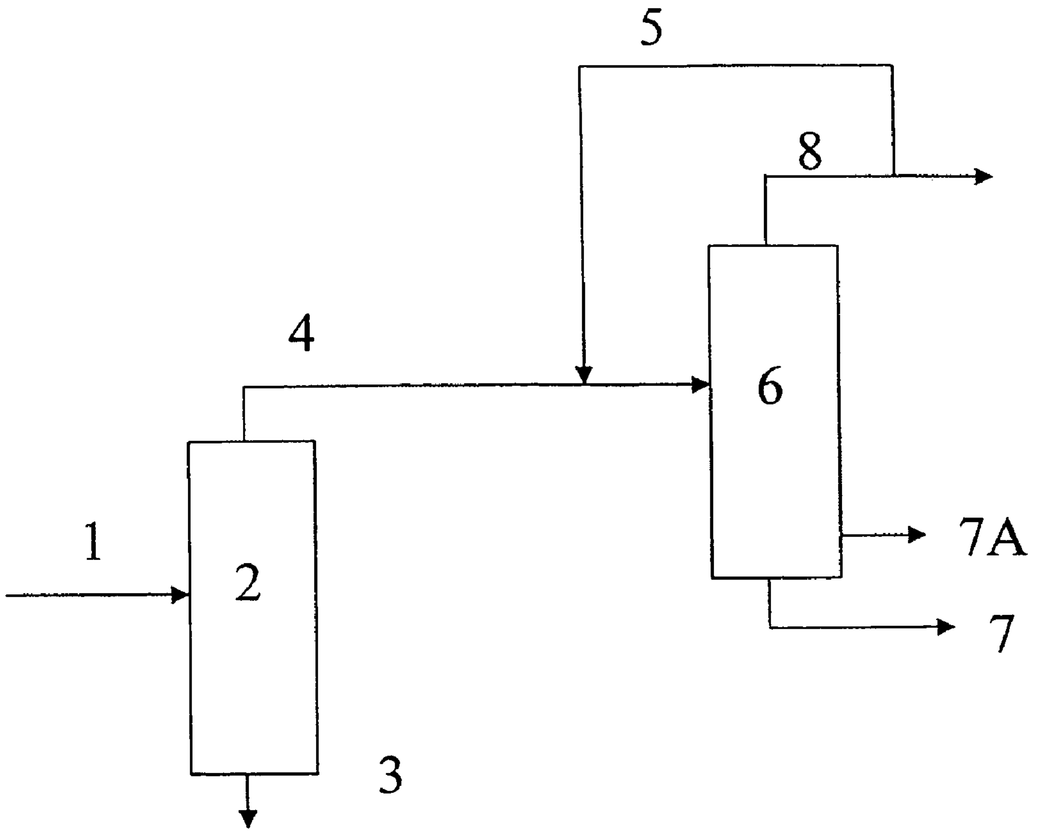
FIG. 2 depicts a block diagram of a plant in which a specific embodiment of the process of the invention can be carried out.

A block diagram of a plant in which the process of the invention can be carried out is shown in FIG. 2. The feed mixture (1) is firstly worked up by distillation in a column (2) to discharge a water-rich stream (3) at the bottom of the column. The distillate stream (4) which has been partly dewatered in this way is then optionally mixed with part (5) of the distillate (8) from the column (6) and introduced into the column (6). In this, the mixture (4) is separated into a bottom product (7) comprising the 2-butanol to be separated off and a top product (8) comprising TBA, water and possibly low boilers. The column (6) is, according to the invention, operated at a pressure different from that in column (2). To obtain 2-butanol containing a low proportion of high boilers, the product can be taken off from the vapor phase of the vaporizer of the column (6) or in gaseous or liquid form as side stream (7A) in the stripping section of the column (6). All or part of the distillate stream (8) can be reused directly as feed to a TBA dissociation.

The feed to the column (6) is, in respect of its water content, in distillation field 2 at the pressure employed in column (6) but in distillation field 1 at the pressure employed in column (2). The water content is less than that described by the boundary B-C in the three-component system SBA/TBA/water. Furthermore, this mixture can contain up to 5% by mass, in particular up to 3% by mass, very particularly preferably up to 2.5% by mass, of further components, for example $C_8$-olefins or -alcohols.

Customary components such as pumps, compressors, valves, heat exchangers and vaporizers are not shown in the block diagrams, but are of course components of a plant.

The following example illustrates the invention without restricting its scope which is defined by the description and the claims.

EXAMPLE

SBA was separated off in a plant of the type shown in FIG. 2 with the stream (5) and (7A) being omitted. The diameter of the column (2) was 50 mm. Metal distillation packing having 12 theoretical plates was installed, and the feed was introduced onto the 7th theoretical plate counted from the top. The diameter of the column (6) was likewise 50 mm. Metal distillation packing having 20 theoretical plates was installed, and the feed was introduced onto the 6th theoretical plate counted from the top. The feed (1) was taken from the industrial plant and used for the experiments. The stream numbers in the following table 1 are the same as those in FIG. 2. The distillate (4) from the column (2) was collected and part of it was used as feed to the second column (6). Components having a concentration below 0.1% by mass in the mixture are generally not shown in the table.

TABLE 1

| Stream number | Stream name | Mass flow [kg/h] | Composition of the stream, in % by mass |
|---|---|---|---|
| 1 | Fresh feed | 1.80 | Water 63.5%<br>TBA 30.2%<br>2-Butanol 4.5%<br>$C_8$-Alcohol 1.7%<br>Other components 0.1% |
| 3 | Waste water | 1.03 | Water 96.9%<br>TBA 0.1%<br>2-Butanol 0.1%<br>C8-Alcohol 2.9% |
| 4 | Dewatered mixture, distillate from column (2) | 0.77 | Water 18.9%<br>TBA 70.3%<br>2-Butanol 10.4%<br>$C_8$-Alcohol 0.1%<br>Other components 0.3% |
| 4 | Dewatered mixture, feed to column (6) | 0.40 | Water 18.9%<br>TBA 70.3%<br>2-Butanol 10.4%<br>C8-Alcohol 0.1%<br>Other components 0.3% |
| 5 | Recycle stream | Omitted | |
| 7 | Bottoms from column (6) | 0.03 | Water 26.3%<br>TBA 1.6%<br>2-Butanol 71.1%<br>$C_8$-Alcohol 0.9%<br>Other components 0.1% |
| 7A | Side stream taken off from column (6) | Omitted | |
| 8 | Distillate from column (6) | 0.37 | Water 18.2%<br>TBA 76.7%<br>2-Butanol 4.8%<br>Other components 0.3% |

The column (2) was operated at 1 bar,abs. and a reflux ratio of 3.5. Column (6) was operated at 0.1 bar,abs. and a reflux ratio of 15.

It can clearly be seen that the process of the invention makes it possible to separate mixtures comprising TBA, SBA and water in such proportions that the composition lies in the distillation field 1 in a simple manner so as to give an SBA fraction which contains less than 2% by mass of TBA. The process of the invention thus achieves the object of the present invention, namely provision of a process by means of which SBA can be separated off from mixtures comprising TBA, SBA and water without significant losses of TBA occurring.

Obviously, numerous modifications and variations of the present invention are possible in light of the above teachings. It is therefore to be understood that within the scope of the appended claims, the invention may be practiced otherwise than as specifically described herein.

This application claims priority to DE 10312917.0 which was filed on Mar. 22, 2003, the entire contents of which are incorporated herein by reference.

The invention claimed is:

1. A process for separating 2-butanol from an industrial mixture which comprises 2-butanol, tert-butanol and water, wherein the proportion by mass of water is greater than the limit concentration of the distillation boundary line connecting an azeotrope of tert-butanol and water; and an azeotrope of 2-butanol and water, comprising (a) separating water from the industrial mixture by distillation to obtain a distillate, wherein the distillate has, in terms of the 2-butanol, tert-butanol and water in the industrial mixture, a proportion by mass of water, which at a pressure, is greater than the limit concentration of the distillation boundary line connecting an azeotrope of tert-butanol and water; and an azeotrope of 2-butanol and water;

(b) subsequently changing the pressure so that the mixture has, in terms of the 2-butanol, tert-butanol and water in the distillate, a proportion by mass of water which is less than the limit concentration of the distillation boundary line connecting the distillation boundary line connecting an azeotrope of tert-butanol and water; and an azeotrope of 2-butanol and water; and (c) subsequently distilling the mixture at the same pressure into a stream comprising 2-butanol and a stream comprising tert-butanol and water.

2. The process as claimed in claim 1, wherein the distillation in (a) is performed on a distillation column.

3. The process as claimed in claim 2, wherein the distillation in (a) is performed at a pressure of from 0.7 to 5 bara.

4. The process as claimed in claim 3, wherein the pressure in (b) and (c) is from 0.05 to not more than 0.7 bara.

5. The process as claimed in claim 3, wherein the pressure in (b) and (c) is from at least 5 to 15 bara.

6. The process as claimed in claim 3, wherein the stream comprising 2-butanol contains less than 2% by mass of tert-butanol.

7. The process as claimed in claim 6, wherein a part of the distillate from (c) is combined with the distillate of (a) and used as a feed to the distillation in (c).

8. The process as claimed in claim 3, wherein the separating of the stream comprising 2-butanol comprises taking a vapor phase of a vaporizer of a column; or a gaseous or liquid as a side stream in a stripping section of the column.

9. The process as claimed in claim 1, wherein the distillation in (a) is performed at a pressure of from 0.7 to 5 bara (bar absolute).

10. The process as claimed in claim 9, wherein the pressure in (b) and (c) is from 0.05 to not more than 0.7 bara.

11. The process as claimed in claim 9, wherein the pressure in (b) and (c) is from at least 5 to 15 bara.

12. The process as claimed in claim 1, wherein the stream comprising 2-butanol contains less than 2% by mass of tert-butanol.

13. The process as claimed in claim 12, wherein the stream comprising 2-butanol contains less than 1.7% by mass of tert-butanol.

14. The process as claimed in claim 12, wherein a part of the distillate from (c) is combined with the distillate of (a) and used as a feed to the distillation in (c).

15. The process as claimed in claim 1, wherein the separating of the stream comprising 2-butanol comprises taking a vapor phase of a vaporizer of a column; or a gaseous or liquid as a side stream in a stripping section of the column.

16. The process as claimed in claim 1, wherein the pressure in (a) is from 0.4 to 5 bara when the proportion of 2-butanol in the industrial mixture is from 0.001 to 30% by mass.

17. The process as claimed in claim 16, wherein the pressure in (b) is from 5 to 15 bara.

18. The process as claimed in claim 16, wherein the pressure in (b) is from 5 to 10 bara.

19. The process as claimed in claim 1, wherein the changing the pressure in (b) comprises increasing the pressure at least 2 times more than the pressure in (a).

20. The process as claimed in claim 1, wherein the stream comprising tert-butanol and water comprises less than 4% by mass of 2-butanol.

21. The process as claimed in claim 1, wherein the stream comprising tert-butanol and water comprises less than 3% by mass of 2-butanol.

* * * * *

UNITED STATES PATENT AND TRADEMARK OFFICE

CERTIFICATE OF CORRECTION

PATENT NO. : 7,125,474 B2
APPLICATION NO. : 10/790706
DATED : October 24, 2006
INVENTOR(S) : Beckmann et al.

It is certified that error appears in the above-identified patent and that said Letters Patent is hereby corrected as shown below:

--(45) **Date of Patent: *Oct. 24, 2006**

(* ) Notice: Subject to any disclaimer, the term of this patent is extended or adjusted under 35 U.S.C. 154(b) by 195 days.

This patent is subject to a terminal disclaimer.--

Signed and Sealed this

Ninth Day of January, 2007

JON W. DUDAS
*Director of the United States Patent and Trademark Office*